United States Patent [19]

Cautilli et al.

[11] 4,387,121
[45] Jun. 7, 1983

[54] METHOD OF MANUFACTURE OF A WATER-PERMEABLE-HYDROPHOBIC MEMBRANE

[75] Inventors: Philip A. Cautilli, Feasterville, Pa.; Edward Wotier, Wayne, N.J.

[73] Assignee: GAF Corporation, New York, N.Y.

[21] Appl. No.: 300,840

[22] Filed: Sep. 10, 1981

Related U.S. Application Data

[63] Continuation of Ser. No. 162,359, Jun. 24, 1980, abandoned.

[51] Int. Cl.$^3$ ............................ B05D 3/02; B05D 5/00
[52] U.S. Cl. .................................. 427/243; 427/389.8; 427/392; 427/393.4; 604/373
[58] Field of Search ............ 427/243, 244, 392, 389.8, 427/393.4; 128/287

[56] References Cited

U.S. PATENT DOCUMENTS 3,882,070 5/1975 Ceska ...................... 260/29.6 MN X
4,112,153 9/1978 Butterworth et al. ........... 427/393.4

Primary Examiner—Evan K. Lawrence
Attorney, Agent, or Firm—Marilyn J. Maue; J. Gary Mohr; Joshua J. Ward

[57] ABSTRACT

A method of making a hydrophobic membrane comprising stabilizing a hydrophobic latex binder by admixture with a fugitive, heat decomposable, hydrophilic surfactant which upon heating yields a hydrophobic residue; applying the latex thus stabilized to a hydrophobic web or substrate of non-woven fibers and then heating the coated web to decompose the surfactant to provide a dry hydrophobic web containing the hydrophobic residue of the surfactant.

9 Claims, No Drawings

METHOD OF MANUFACTURE OF A WATER-PERMEABLE-HYDROPHOBIC MEMBRANE

This is a continuation of application Ser. No. 162,359, filed June 24, 1980, abandoned.

BACKGROUND OF THE INVENTION

1. Field of the Invention

This invention relates to a method of manufacturing a water-permeable hydrophobic substrate and, more particularly, to the use of a transitory hydrophilic surfactant in an aqueous dispersion of a hydrophobic binder, depositing the binder on the substrate and negating the hydrophilicity of the surfactant.

2. Brief Description of the Prior Art

Water based binder systems are preferred because of the low cost associated with using water as a solvent, as compared to using, for example, an organic solvent such as ethanol. Water presents no recovery or pollution problem and, thus further contributes to its value as a solvent.

However, there is a conflict in that where an end product having a hydrophobic quality is produced through the use of a hydrophobic binder such as styrene-butadiene copolymers, since the styrene-butadiene latex must be free of surfactants or at least sufficiently surfactant-free so as not to interfere with the hydrophobicity of the end product.

By way of example, in the case of a disposable diaper, an absorbent wadding would be produced as disclosed in U.S. Pat. No. 3,180,335, the disclosure of which is herein incorporated by reference. The web is a compliant, soft-feeling, porous, hydrophobic paper or non-woven fabric member. An example of a non-woven fabric sheet which has been found to function well on diapers is one which comprises 1.5 to 3 denier rayon and contains approximately 20–35% thermoplastic binder (as, for example, copolymers of an ester of acrylic acid such as is sold by the Rohm & Haas Company and identified as B-15), and having a weight of about 15–19 grams per square yard. The patent discloses that, for best results in processing, such a sheet, surfactants should be minimal in the binder emulsion and avoided in the final bath. The patent further discloses the use of a flexible waterproof back sheet desirably comprising a 0.001" thick low density, opaque polyethylene web which is preferably larger than the corresponding dimensions of the pad.

SUMMARY OF THE INVENTION

The invention concerns the manufacture of a hydrophobic membrane by stabilizing a hydrophobic latex binder by inclusion of a neutralized, heat decomposable, fugitive hydrophilic surfactant, such as a fatty acid ammonium salt, which upon heating yields a hydrophobic residue; applying the stabilized latex to a substrate or non-woven mat of synthetic fibers and then heating the coated mat to dry same leaving the hydrophobic residue from the surfactant in the binder applied to the dried mat.

THE DESCRIPTION OF THE PREFERRED EMBODIMENTS

The object of the invention will become apparent from the following description.

The use of the fugitive surfactant system of the instant invention is primarily described in conjunction with the production of disposable diapers of the type described in U.S. patents such as U.S. Pat. Nos. 3,196,874 and 3,180,335. However, this is by way of convenience rather than by way of limitation, and the process has similar utility in connection with the production of hydrophobic substrates from waterbased latexes, for other uses, as for example, feminine napkins and tampons, tablecloths and upholestry fabric.

A non-woven textile fabric can be readily prepared using papermaking procedures aand having a high hydrophobicity level so as to have a high stain-resistance level. Such textile materials find substantial usage as upholestry fabrics.

U.S. Pat. No. 3,196,874, the disclosure of which is herein incorporated by reference discloses that in a disposable diaper, the absorbent pad comprises a layer of cellulosic fiber or any other material offering suitable fluid absorbent characteristics, it being the function of the pad to provide the required softness and bulk in addition to its primary function as the major fluid absorbent element. An overlying protective sheet may consist of a non-woven web of synthetic fibers, such as nylon or rayon fibers maintained in bonded engagement, said webbing being known in the art. The sheet is positioned for direct contact with the body of an infant, thus, should be soft and flexible while also being substantially nonadherent to human skin when either dry or wet.

Non-bonded webs formed of synthetic fibers, such for example as nylon or Dacron fibers, while somewhat hydrophobic in character, are particularly adapted for use as the overlying sheet. When placed contiguous to an underlying element of substantial hydrophilic character such as creped wadding or fluff, the capillary attraction exerted by the underlying element sufficiently counteracts the hydrophobic characteristics of a relatively thin overlying sheet. Hence fluid flow therethrough to the underlying element is permitted, but the overlying sheet remains comparatively dry and non-adherent to an infant's body. The combination of the light weight and comparatively thin overlying protective sheet of the above characteristics and the immediately underlying relatively bulky element of highly fluid absorbent material results in a substantial reduction in diaper rash due to the comparative dryness of the overlying sheet during use. The combination also minimizes the tendency of the diaper cling to the skin of the wearer, and the attendant discomfort. The underlying fluid impervious sheet may, for example, be of polyethylene sheet stock, or the like, which offers the desirable characteristics of flexibility and softness while serving its primary function as a fluid impervious envelope for the associated diaper elements.

The increase in the hydrophobicity of the water-permeable sheet is achieved through the use of a fugitive surfactant which is highly hydrophilic when a part of the latex system and hydrophobic, or at least non-hydrophilic, to the extent that it is present in the final product.

The term "fugitive surfactant" as employed herein is intended to describe a short-lived or transitory surfactant, which is perishable and disappears upon the occurrence of a predetermined event, such as the application of heat.

The resultant products made by the process of the instant invention would be termed "water-repellant" as contrasted with "waterproof". A waterproof fabric is defined as one in which the pores of intersices between fibers and between yarns are filled with appropriate substances which cause the fabric to have a continuous surface and very small air or water vapor permeability. A water-repellant fabric is one whose fibers are usually coated with a hydrophobic-type compound and whose pores are not filled in the course of the treatment. The latter types of fabrics are quite permeable to air and water vapor and water can be drawn through the pores, as for example, by the action or attraction of a hygroscopic agent.

In the production of hydrophobic membranes, a typical method of application is to prepare a non-woven mat of synthetic fibers, such as nylon, rayon, polyvinyl acetate, polyester, polyethylene or polypropylene fibers. A latex, such as styrene-butadiene rubber, an acrylic latex, or the like, is then applied to the non-woven mat, typically by means of a roller or plurality of rollers and the product is then oven-dried. The fibers of the non-woven mat are then bound together by means of the resin of the latex.

In production, latexes having a high hydrophobicity have a tendency to clog or coagulate on the roller during the step of application of the latex to the non-woven mat by means of the roller. In this step, the latex is subjected to a sheer action due to the compression effect of the roller and is not uncommon to see excessive build-up of latex particles which are caused by a coagulation or aggregated polymer. The use of a hydrophilic surfactant works well to stabilize the latex and prevent the coagulation from occurring. However, a hydrophilic surfactant will impart a hydrophilic nature to the final product, therefore, negating the valve of the hydrophobic polymer. It is desired to achieve a balance between stabilizing the latex and retaining the hydrophobicity of the web. In accordance with the present invention, latexes, such as employed in the textile industry, can be stabilized through the use of a fugitive surfactant. The surfactant is employed in preferably ammonium oleate because, at room temperature, it is an oil and, therefore, is most readily employed. However, other heat decomposible surfactants could be used, such as other fatty acid derived surfactants, such as the ammonium salt of stearic acid, palmitic acid or lauric acid. After the application of heat in the oven and the driving off of the ammonia, the residue of the surfactant is a hydrophobic group and, therefore, does not contradict or compromise the hydrophobicity of the membrane. Consequently, there is no reasonable limitation in the amount of surfactant used in the processing of the latex and copious quantities can be employed with no adverse effect in the final product. The latexes are not narrowly critical and the commonly employed latexes, such as acrylics, vinyls, SBR, etc., can be employed in the instant system provided they are initially hydrophobic.

The instant invention provides the unique advantage of permitting the use of a water-base latex, thus providing extreme convenience of manufacture of the product, while nevertheless, yielding an extremely hydrophobic end product.

The synthetic resin fibers which can be employed include polyolefins, such as polyethylene and polypropylene, polyesters, and cellulosics.

The latex may, in principle, be any dispersion of a synthetic polymeric material obtained by the emulsion polymerization of ethylenically unsaturated monomers, such as a latex of polyvinyl chloride or polyvinylidene chloride; a latex of a homopolymer or copolymer of diolefins with 4 to 8 carbon atoms, for instance: 1,3-butadiene, isoprene, 1,4-dimethylbutadiene-1,3 and 1,3-dimethylbutadiene-1,3 in combination, if desired, with another monomer such as styrene, methylacrylate, ethylacrylate, methyl methacrylate, ethyl methacrylate, acrylonitrile, N-methylol(meth)acrylamide or isobutene; a latex of a polymer or copolymer of one or more alkyl acrylates or alkyl methacrylates, in combination, if desired, with another monomer such as styrene, vinyl chloride or vinylidene chloride; and a latex of a polymer of chloroprene or a mixture of the above-mentioned latices.

The only critical limitation with respect to the latex is that it yields a hydrophobic binder. It should be noted that although the use of a fugitive surfactant, such as ammonium oleate, provides compatibility between the hydrophobic polymeric material and the water during processing, after oven drying, the residual portion of the surfactant is hydrophobic. Thus, the hydrophobicity of the membrane can actually be enhanced by using large quantities of surfactant.

The latex of the invention, may be applied to fiber webs made from very widely differing materials, for instance, rayon fibers, shredded or non-shredded cellulose, polyester fibers, polyamide fibers, polypropylene fibers, glass fibers and other current fibers suitable to be processed on the paper-making machine, or mixtures of the above-mentioned fibers. The use of fiber webs consisting entirely or partly of non-shredded cellulose may mean a considerable saving in cost.

The fibers either should not be hydrophilic or should be totally coated with binder so as to present a hydrophobic surface to the absorbent pad or other water laden surface with which it is used.

TABLE I

| | Pad-Roll Stability | |
|---|---|---|
| Binder Systems | Time-Run | Ratings & Observations |
| Rhoplox HA-8[2] | 15 minutes | Excellent - no build-up. |
| National Starch 2833[3] | 15 minutes | Good - slight waxy build-up in 8–10 mins. Did not worsen thru 15 minutes. |
| Crosslinkable Sty/BD/MAA/ AM/NMA | | Fair-Med - build-up in 6 min. Continued to worsen thru 15 minutes. |
| Crosslinkable Sty/BD/MAA/ AM/NMA ½pt. Ammonium Oleate | 15 minutes | Very Good - slight build-up in 10–12 mins. Did not worsen thru 15 minutes. |
| Crosslinkable Sty/BD/MAA/ AM/NMA 1 pt. Ammonium Oleate | 15 minutes | Excellent - no build-up. |

[1]All latexes cut 1:1 vol. with water before tests run.
[2]Trademark of the Rohm & Haas company for aqueous dispersions of acrylic copolymers.
[3]Trademark for a polyvinyl acetate aqueous dispersions.

The hydrophobic polymer composition of Table 1 was styrene, 1,3-butadiene/methacrylic acid/N-methylolacrylamide in a 39/57/1/3.0 ratio.

The latex had a 46.1% total solids content, a Brookfield viscosity of 124 cps, a surface tension of 63 dy/cm and a pH adjusted to 8.5 with $NH_3$ only.

In preparing the composition, the ingredients were as follows:

|  | Wt. % of Total (as is) | % Active |
|---|---|---|
| 1. Hampene 100 | 0.075 | 38 |
| 2. Seed Polymer Latex | 3.198 | 42 |
| 3. Oleic Acid | 1.103 | 100 |
| 4. Ammonium Persulfate | 0.318 | 100 |
| 5. Styrene | 17.183 | 100 |
| 6. 1,3-Butadiene | 25.774 | 100 |
| 7. Methacrylic Acid | 0.448 | 100 |
| 8. 4P Mercaptan | 0.204 | 100 |
| 9. N—Methylolacrylamide | 2.86 | 48 |
| 10. Water (deionized) | 49.046 | — |
| 11. t-butyl hydroperoxide | 0.393 | 70 |
| 12. Erythorbic Acid | 0.02 | 100 |

When desired, the batch was adjusted to the pH in the 8.5 to 9.0 range with the required quantity of ammonia.

The batch is then drained and filtered.

After a two hour hold at 185° F., chemical stripping additives (3 grams tertiary-butyl hydroperoxide (70%) and 7 grams of isopropyl alcohol) were added, followed by an addition of 10 grams of erythobic acid (5% solution).

After an additional one hour hold at 185° F., the resultant latex was cooled to ambient temperature.

Oleic acid was added in a desired concentration and the mixture agitated for 15 minutes to provide thorough mixing.

PROCEDURE FOR PRODUCING LATEX

A clean reactor was charged with 633 grams deionized water, 1.9 grams Hampene 100 (38%) an EDTA chelating agent, 81.5 grams of the seed polymer latex (42%) and 2.85 grams of oleic acid. A vacuum was drawn to eliminate air, the ingredients agitated and the reactor heated to the polymerization temperature of 185° F.

The monomer premix of 438 grams styrene, 657 grams 1,3-butadiene, 11.4 grams methacrylic acid and 5.2 grams of a tertiary dodecyl mercaptan chain transfer agent sold under the designation 4P Mercaptan were gradually pumped into the reactor until a positive pressure was achieved, at which time a reactor initiator solution of 100 grams of deionized water and 2.5 ammonium persulfate was entirely charged to the reactor. The gradual monomer feed was continued and the gradual feeding of a crosslinking solution of 72.9 grams N-methylol-acrylamide (48%) as well as a gradual feed initiator solution of 365 grams deionized water and 5.6 grams of ammonium persulfate were commenced and maintained for four hours at 185° F.

In the prior art, as exemplified by the teachings of U.S. Pat. No. 3,882,070, N-methylolacrylamide (NMA) is recognized as having value in latex stabilization. In the process of the aforenoted patent, monomer, persulfate initiator and NMA are added simultaneously in two steps. The water soluble NMA rapidly polymerizes to a soap, followed by polymerization of the water insoluble butadiene and styrene. Thus, at best, minimal, random poly NMA-butadiene-styrene interaction occur. By way of contrast, the gradual addition of NMA over a substantial and extended portion of the polymerization produces a regular polymer chain with NMA groups at regular intervals extending from the chain.

Among other features, NMA contributes to the ability of the resultant fabric to be drycleaned with solvents, such as perchlorethylene.

A carboxylic acid, preferably methacrylic acid, is employed in the system so as to provide, in combination with the sulfate end groups of the persulfate initiator stabilization during polymerization. This eliminates the need to front load the reaction with NMA in the aforenoted manner and to achieve NMA availability throughout the polymerization process as well as better curing.

TABLE II

| Deaper Facing Testing* | | |
|---|---|---|
| Binder Systems | Strike-Thru (seconds) | Dryness (grams) |
| (1) National Starch 2833 | 12.6 | 0.082 |
| (2) Crosslinkage Styrene/Butadiene/ Methacrylic Acid Latex ½ pt. Ammonium Oleate | 12.0 Second | Too hydrophobic to run |

Testing Parameters
Application: Saturation technique
Substrate: 100% carded polyester
Add-On: 43 ± 3.0
Cure: 2' @ 300° F. Air-Draft Oven
*Run via strike-thru/dryness apparatus
Current Specs - S.T. <3 seconds ⎫
                                    ⎬ As formulated
Dryness <.3 grams                   ⎭

The binder system of run (2) being more hydrophobic than the commercial material can be formulated to achieve extremely fast strike-through values and yet exhibit lower dryness values (wet-back) than formulated commercial binders.

Strike-through value control can most readily be achieved by varying the ratio of binder to oleate. In a pre-formulated system, control can be achieved through the addition of a small quantity of a hydrophilic agent.

The fibers can be wettable cellulosic fiber since the binder is capable of delivering any desired degree of hydrophobicity. In the case of feminine hygiene products, water and moisture impermeability is typically desired. While this quality can readily be achieved through the use of a solid sheet rather than a woven or non-woven fabric, the feel of the fabric commonly termed "Hand" cannot readily be provided by a non-porous sheet.

It is thus seen that the use of a fugitive surfactant facilitates the customizing of the end result to any desired extent, by simply varying the concentration of the ammonium oleate or by offsetting the hydrophobicity to a predeterminable extent with a wetting agent. By way of contrast, in conventional systems, the maximum hydrophobicity is limited by the requirements of the coating step and the binder must be selected for compatibility with processing techniques rather than desired end result or else processing techniques rather than desired end result or end processing problems must be tolerated. In the instant system, the use of a fugitive surfactant eliminates the processing difficulties normally encountered with aqueous solutions of hydrophobic resins while providing higher levels of hydrophobicity than otherwise considered feasible to attain.

Further, the use of a "maximum" hydrophobicity enables a single binder to have more universal applicability since hydrophobicity can be readily decreased without altering the binder formulation. By way of contrast, the hydrophobicity of, for example, National Starch 2833, cannot be increased without adversely affecting the problem of resin build-up on rollers during the coating step.

An accelerated stability test was run for the purpose of predicting long-term stability under actual plant conditions. The Pad-Roll stability test was run on a three roll Butterworth padder set at 20 pounds pressure and run at 40 rpm. The test compared two binder systems which are currently in commercial use in hydrophobic members, with a high hydrophobic binder with and without a fugitive surfactant.

This concept has been employed by adding the fugitive soap to the polymerized latex. In the case of a hydrophobic system, hydrophilic surfactants are employed for stabilization during polymerization. The fugitive surfactant can then be added and the system stabilized until a film is formed. The problem encountered in forming a highly hydrophobic system is that the need for stabilization during polymerization is enhanced while the need to be hydrophilic surfactant-free in the final product is simultaneously and incompatibly enhanced. It has been found that adding the fugitive surfactant to the monomer system prior to polymerization greatly enhanced the quality of the final product by providing optimum mixing since it is easier to mix the surfactant with monomers than with a relatively long chain polymer. Moreover, it would appear that the surfactant bonds to the polymer chain during polymerization, thus maximizing the effectiveness of the surfactant, although it is not intended to be bound to any particular theory of operation and the theoretical explanation is presented by way of providing maximum disclosure rather than by way of limiting the invention.

In the polymerization of carboxylated monomers, the fugitive surfactant cannot be employed as a stabilizer during polymerization because the high pH required for the ammonia or amine form of the fugitive surfactant is incompatible with the low pH required in the polymerization process.

Thus, heretofore, the need for stabilization during the polymerization resulted in the presence of some hydrophilic groups in the final polymer and the presence of carboxylic acid groups in the monomer precluded the use of an amine or ammonia type of fugitive surfactant.

The polymerization initiator is employed as a dual function initiator-stabilizer and the methacrylic acid functions as a monomer and provides additional stabilizer groups. The styrene-butadiene system is so highly hydrophobic that polymerization in an aqueous medium is not feasible in the absence of fine size particles or seeds on which the copolymers can grow. The seed polymer is preferably a styrene-butadiene copolymer conveniently in the ratio of about 3 to 1 styrene to butadiene, which the ratio is not narrowly critical and can be varied as desired. A particle size of less than 10 microns is preferred.

What is claimed is:

1. The method of making a hydrophobic membrane, comprising the steps of:
    (a) providing a latex which comprises water and a hydrophobic binder;
    (b) stabilizing the latex with a sufficient quantity of a heat decomposable hydrophilic fugitive surfactant to preclude coagulation of the binder, said surfactant capable of decomposing under heat to yield a hydrophobic residue of the surfactant;
    (c) coating a non-woven mat with the stabilized latex and;
    (d) heating to dry the non-woven mat which has been coated with the stabilized latex while simultaneously decomposing the fugitive surfactant to form a hydrophobic membrane containing the hydrophobic residue of the surfactant.

2. The method of claim 1, wherein the hydrophobic binder is a synthetic polymer obtained by the emulsion polymerization of ethylenically unsaturated monomers.

3. The method of claim 1, wherein the non-woven mat is formed of cellulose, polyester or polyolefin fibers or combinations thereof.

4. The method of claim 1, wherein the fugitive surfactant is ammonium carboxylate.

5. The method of claim 4, wherein the latex is formed by mixing a long chain carboxylic acid having at least six carbons in the chain with styrene and butadiene monomer, polymerizing the monomers to form a hydrophobic polymeric binder, and neutralizing the acid with ammonia to form said ammonium carboxylate.

6. The method of claim 5, wherein said latex is prepared by polymerizing said carboxylic acid, styrene and butadiene monomer on a prepolymer seed in the presence of a persulfate polymerization initiator and with the gradual addition of N-methylolacrylamide to form polymer chains having uniform monomer distribution.

7. The method of claim 1, wherein the surfactant is ammonium oleate.

8. The method of claim 1, wherein the binder is a carboxylated styrene-butadiene copolymer.

9. The method of claim 8, wherein binder copolymer further includes copolymerized amide or methylolamide moieties.

* * * * *